United States Patent
Gerstenblith et al.

(10) Patent No.: US 10,772,716 B2
(45) Date of Patent: Sep. 15, 2020

(54) METHODS FOR PROMOTING HEALING OF TISSUE

(71) Applicant: THE JOHNS HOPKINS UNIVERSITY, Baltimore, MD (US)

(72) Inventors: Gary Gerstenblith, Reisterstown, MD (US); Jason Benkoski, Ellicott City, MD (US); George Coles, Baltimore, MD (US); Chao-Wei Hwang, Ellicott City, MD (US); Peter Johnston, Baltimore, MD (US); Gordon Tomaselli, Lutherville, MD (US); Robert G. Weiss, Hunt Valley, MD (US); Steven P. Schulman, Reisterstown, MD (US); Jeffrey A. Brinker, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/281,620

(22) Filed: Feb. 21, 2019

(65) Prior Publication Data

US 2019/0314416 A1    Oct. 17, 2019

Related U.S. Application Data

(63) Continuation of application No. 15/467,455, filed on Mar. 23, 2017, now abandoned, which is a
(Continued)

(51) Int. Cl.
*A61F 2/02* (2006.01)
*A61L 27/38* (2006.01)
(Continued)

(52) U.S. Cl.
CPC ............ *A61F 2/022* (2013.01); *A61K 9/0024* (2013.01); *A61K 35/28* (2013.01); *A61K 35/545* (2013.01);
(Continued)

(58) Field of Classification Search
CPC .... A61K 35/28; A61K 9/0024; A61K 35/545; A61L 29/16; A61L 29/146; A61L 31/10;
(Continued)

(56) References Cited

U.S. PATENT DOCUMENTS 5,011,472 A    4/1991  Aebischer et al.
5,201,728 A    4/1993  Giampapa
(Continued)

FOREIGN PATENT DOCUMENTS

WO    WO-2009061382 A2 *  5/2009  ......... G01N 33/6887

OTHER PUBLICATIONS

Hare, et al., A randomized, double-blind, placebo-controlled, dose-escalation study of intravenous adult human mesenchymal stem cells (prochymal) after acute myocardial infarction. J Am Coll Cardiol. Dec. 8, 2009;54(24):2277-86.
(Continued)

*Primary Examiner* — Amber R Stiles
(74) *Attorney, Agent, or Firm* — Johns Hopkins Technology Ventures

(57) ABSTRACT

A method for promoting healing of tissue by delivering a bioreactor into a subject is provided. The bioreactor is an enclosed housing with paracrine factor producing cells enclosed within the housing. The housing is impermeable to the paracrine factor producing cells, impermeable to immunological cells outside of the housing, and permeable to paracrine factors produced by the paracrine factor producing cells. The paracrine factors produced by the paracrine factor producing cells are released out of the housing to promote healing of the tissue.

24 Claims, 9 Drawing Sheets

SIMPLIFIED CATHETER-BASED TEMPORARY STEM CELL BIOREACTOR

Related U.S. Application Data continuation of application No. 13/251,910, filed on Oct. 3, 2011, now abandoned.

(60) Provisional application No. 61/388,778, filed on Oct. 1, 2010.

(51) Int. Cl.

| | |
|---|---|
| A61L 27/54 | (2006.01) |
| A61K 35/545 | (2015.01) |
| A61L 29/00 | (2006.01) |
| A61L 29/16 | (2006.01) |
| C12N 5/0775 | (2010.01) |
| A61K 35/28 | (2015.01) |
| A61K 9/00 | (2006.01) |
| A61L 29/14 | (2006.01) |
| A61L 31/10 | (2006.01) |
| A61L 31/14 | (2006.01) |
| A61L 31/16 | (2006.01) |
| A61L 27/16 | (2006.01) |
| A61L 27/28 | (2006.01) |
| A61L 27/56 | (2006.01) |

(52) U.S. Cl.
CPC ............ *A61L 27/16* (2013.01); *A61L 27/28* (2013.01); *A61L 27/3834* (2013.01); *A61L 27/54* (2013.01); *A61L 27/56* (2013.01); *A61L 29/00* (2013.01); *A61L 29/005* (2013.01); *A61L 29/146* (2013.01); *A61L 29/16* (2013.01); *A61L 31/10* (2013.01); *A61L 31/145* (2013.01); *A61L 31/146* (2013.01); *A61L 31/16* (2013.01); *C12N 5/0663* (2013.01); *A61L 2300/30* (2013.01); *A61L 2300/42* (2013.01); *A61L 2300/64* (2013.01); *A61L 2430/20* (2013.01); *C12N 2533/30* (2013.01)

(58) Field of Classification Search
CPC ...... A61L 31/145; A61L 31/146; A61L 31/16; A61L 29/005; A61L 27/16; A61L 27/28; A61L 27/56; A61L 29/00; A61L 27/3834; A61L 27/54; A61L 2300/30; A61L 2300/42; A61L 2430/20; A61L 2300/64; A61F 2/022; C12N 5/0663; C12N 2533/30

See application file for complete search history.

(56) References Cited

U.S. PATENT DOCUMENTS

| | | | |
|---|---|---|---|
| 5,770,193 A | 6/1998 | Vacanti et al. | |
| 5,770,417 A | 6/1998 | Vacanti et al. | |
| 5,916,554 A * | 6/1999 | Dionne | A61K 9/0024 424/422 |
| 6,479,066 B1 | 11/2002 | Harpstead | |
| 6,758,828 B2 | 7/2004 | Hammer et al. | |
| 7,044,965 B1 | 5/2006 | Spielberg | |
| 7,195,774 B2 | 3/2007 | Carvalho et al. | |
| 2001/0044413 A1 | 11/2001 | Pierce et al. | |
| 2002/0081726 A1 | 6/2002 | Russell et al. | |
| 2005/0177106 A1 | 8/2005 | Naimark et al. | |
| 2005/0209556 A1 | 9/2005 | Tresco et al. | |
| 2005/0271697 A1 * | 12/2005 | Litvack | A61F 2/91 424/423 |
| 2006/0034808 A1 * | 2/2006 | Mizuno | C12N 5/0068 424/93.7 |
| 2006/0136049 A1 * | 6/2006 | Rojo | A61F 2/82 623/1.42 |
| 2006/0200083 A1 * | 9/2006 | Freyman | A61M 5/14526 604/181 |
| 2007/0042015 A1 | 2/2007 | Berry et al. | |
| 2007/0141106 A1 | 6/2007 | Bonutti et al. | |
| 2008/0050347 A1 | 2/2008 | Ichim | |
| 2010/0184183 A1 * | 7/2010 | Schussler | A61L 27/24 435/177 |
| 2011/0028945 A1 | 2/2011 | Amodei et al. | |
| 2011/0098799 A1 | 4/2011 | Treacy et al. | |
| 2017/0245976 A1 * | 8/2017 | Gerstenblith | A61F 2/022 |

OTHER PUBLICATIONS

Abdel-Latif, et al., Adult bone marrow-derived cells for cardiac repair: a systematic review and meta-analysis. Arch Intern Med. May 28, 2007;167(10):989-97.

Johnston, et al., Engraftment, differentiation, and functional benefits of autologous cardiosphere-derived cells in porcine ischemic cardiomyopathy. Circulation. Sep. 22, 2009;120(12):1075-83, 7 p following 1083.

Williams, et al., Intramyocardial stem cell injection in patients with ischemic cardiomyopathy: functional recovery and reverse remodeling. Circ Res. Apr. 1, 2011;108(7):792-6.

Chavakis, et al., Enhancing the outcome of cell therapy for cardiac repair: progress from bench to bedside and back Circulation. Jan. 19, 2010;121(2):325-35.

Terrovitis, et al., Assessment and optimization of cell engraftment after transplantation into the heart. Circ Res. Feb. 19, 2010;106(3):479-94.

Gnecchi, et al., Paracrine action accounts for marked protection of ischemic heart by Akt-modified mesenchymal stem cells. Nat Med. Apr. 1, 2005; 1(4):367-8.

Gnecchi, et al., Paracrine mechanisms in adult stem cell signaling and therapy. Circ Res. Nov. 21, 2008;103(11)1204-19.

Chimenti, et al., Relative roles of direct regeneration versus paracrine effects of human cardiosphere-derived cells transplanted into infarcted mice. Circ Res. Mar. 19, 2010;106(5):971-80.

Weber, et al., Expansion of human mesenchymal stem cells in a fixed-bed bioreactor system based on non-porous glass carrier—part A: inoculation, cultivation, and cell harvest procedures. Int J Artif Organs. Aug. 2010;33(8):512-25.

Kresnowati,. et al., Model-based analysis and optimization of bioreactor for hematopoietic stem cell cultivation. Bioprocess Biosyst Eng. Jan. 2011;34(1):81-93.

Korbling, et al., Adult stem cells for tissue repair—a new therapeutic concept? N Engl J Med. Aug. 7, 2003;349(6):570-82.

Orlic, et al., Bone marrow cells regenerate infarcted myocardium. Nature. Apr. 5, 2001;410(6829):701-5.

Pittenger, et al., Multilineage potential of adult human mesenchymal stem cells. Science. Apr. 2, 1999;284(5411):143-7.

Toma, et al., Human mesenchymal stem cells differentiate to a cardiomyocyte phenotype in the adult murine heart. Circulation. Jan. 1, 2002;105(1):93-8.

Beltrami, et al., Adult cardiac stem cells are multipotent and support myocardial regeneration. Cell. Sep. 19, 2003;114(6):763-76.

Smith, et al., Regenerative potential of cardiosphere-derived cells expanded from percutaneous endomyocardial biopsy specimens. Circulation. Feb. 20, 2007;115(7):896-908.

Bergmann, et al., Evidence for cardiomyocyte renewal in humans. Science. Apr. 3, 2009;324(5923):98-102.

Abraham, M. Roselle, and Gary Gerstenblith. "Preconditioning stem cells for cardiovascular disease: an important step forward." Circ Res. 2007;100:447-449.

Gerstenblith, Gary, and Robert G. Weiss. "Long-term effects of stem cell transplantation in the postinfarct heart: benefits and mechanisms." American Journal of Physiology-Heart and Circulatory Physiology 298.5 (2010): H1308-H1309.

Terrovitis,J. et al, "Magnetic resonance imaging overestimates ferumoxide-labeled stem cell survival after transplantation in the heart", Circulation. Mar. 25, 2008;117(12):1555-62.

Erickson, Harold P. "Size and shape of protein molecules at the nanometer level determined by sedimentation, gel filtration, and electron microscopy." Biological procedures online 11.1 (2009): 32.

(56) References Cited

OTHER PUBLICATIONS

Lai, Ruenn Chai, et al. "Exosome secreted by MSC reduces myocardial ischemia/reperfusion injury." Stem cell research 4.3 (2010): 214-222.
Timmers, Leo, et al. "Reduction of myocardial infarct size by human mesenchymal stem cell conditioned medium." Stem cell research 1.2 (2008): 129-137.
Kang, Dukjin, et al. "Proteomic analysis of exosomes from human neural stem cells by flow field-flow fractionation and nanoflow liquid chromatography-tandem mass spectrometry." Journal of proteome research 7.8 (2008): 3475-3480.
Lai, Ruenn Chai, et al. "Derivation and characterization of human fetal MSCs: an alternative cell source for large-scale production of cardioprotective microparticles." Journal of molecular and cellular cardiology 48.6 (2010): 1215-1224.
Hong, Kyung U., and Roberto Bolli. "Cardiac stem cell therapy for cardiac repair." Current treatment options in cardiovascular medicine 16.7 (2014): 324.
Sanganalmath, Santosh K., and Roberto Bolli. "Cell therapy for heart failure: a comprehensive overview of experimental and clinical studies, current challenges, and future directions." Circulation research 113.6 (2013): 310-834.

\* cited by examiner

FIGURE: CATHETER-BASED TEMPORARY STEM CELL BIOREACTOR

METHODS FOR PROMOTING HEALING OF TISSUE

CROSS-REFERENCE TO RELATED APPLICATIONS

This application is a continuation of U.S. patent application Ser. No. 15,467,455, filed on Mar. 23, 2017, which is a continuation of U.S. patent application Ser. No. 13/251,910, filed on Oct. 3, 2011, which claims priority to U.S. Provisional Patent Application No. 61/388,778, filed on Oct. 1, 2010.

BACKGROUND

Heart muscle damage is the final common pathway for most forms of cardiovascular disease and when extensive can impair quality of life and shorten survival. The most common cause is obstruction in coronary arteries, but the heart as well as other organs can be damaged by trauma, toxins, and infections. There are no currently approved therapies to generate new myocardium, or heart muscle. Stem cells have been administered intravenously (Hare et al. *J Am Coll Cardiol*. Dec. 8, 2009; 54(24):2277-2286), via infusion into the coronary arteries (Abdel-Latif et al. *Arch Intern Med*. May 28, 2007; 167(10):989-997, Johnston et al. *Circulation*. Sep. 22, 2009; 120(12):1075-1083) and by injection into the heart muscle itself (Williams et al. *Circ Res*. Apr. 1, 2011; 108(7):792-6). The results in terms of improved muscle function, however, have been very limited, possibly because of early "washout" (short duration of viable cells at the target site because of blood flow), the hostile environment into which the cells are delivered, and immunologic attack (Chavakis et al. *Circulation;* Jan. 19, 2010; 121(2):325-335, Terrovitis et al. *Circ Res. Feb.* 19, 2010; 106(3):479-494). Biomolecules released by the stem cells, called paracrine factors, may be responsible, in part, for their benefit (Gnecchi et al. *Nat Med*. April 2005; 11(4):367-368, Gencchi et al. *Circ Res. Nov.* 21, 2008; 103(11):1204-1219, Chimenti et al. *Circ Res. Mar.* 19, 2010; 106(5):971-980).

An embodiment relates to an implantable bioreactor comprising a housing comprising cells which produce paracrine factors in situ; wherein the housing comprises a barrier that shields the enclosed cells from immunological attack and permits the transfer of paracrine factors out of the housing. The implantable bioreactor can be for systemic or local delivery of paracrine factors. The implantable bioreactor housing can be in the form of a pouch, semi-permeable membrane, a cellular microenclosure or a matrix gel. The bioreactor can be optionally adhered to a medical device.

Another embodiment relates to a method for promoting healing of injured myocardium. The method comprises percutaneously delivering a bioreactor to the subject. The bioreactor comprises an enclosed housing and paracrine factor producing cells enclosed within the housing. The housing is impermeable to the paracrine factor producing cells, impermeable to immunological cells outside of the housing, and permeable to paracrine factors produced by the paracrine factor producing cells. The paracrine factors produced by the paracrine factor producing cells are released out of the housing to promote healing of the injured myocardium.

Another embodiment relates to a method for promoting healing of tissue in a subject. The method comprises delivering a bioreactor into a subject. The bioreactor comprises an enclosed housing and paracrine factor producing cells enclosed within the housing. The housing is impermeable to the paracrine factor producing cells, impermeable to immunological cells outside of the housing, and permeable to paracrine factors produced by the paracrine factor producing cells. The paracrine factors produced by the paracrine factor producing cells are released out of the housing to promote healing of the tissue.

Another embodiment relates to another method for promoting healing of tissue in a subject. The method comprises percutaneously delivering a bioreactor into the subject. The bioreactor is mounted on a catheter having at least one lumen and an infusion port. The at least one catheter lumen connects the infusion port with the housing lumen. The bioreactor comprises an enclosed housing having a lumen. The housing has pores of sufficient size to restrict the entry of immunological cells into the housing, restrict the egress of cells out of the housing, and allow the release of paracrine factors out of the housing. The method further includes introducing cells through the infusion port and into the housing lumen permitting the release of paracrine factors out of the housing to promote healing of the tissue.

DETAILED DESCRIPTION

Figure 1:
FIG. 1: Miniature bioreactor for in vitro paracrine factor production and cell viability experiments.

Clinical trials using intra-coronary and intra-myocardial injection of stem cells in an attempt to heal and regenerate infarcted myocardium have produced modest results to date (Chavakis et al. *Circulation;* Jan. 19, 2010; 121(2):325-335, Terrovitis et al. *Circ Res. Feb.* 19, 2010; 106(3):479-494). Potential reasons for the modest results may be related to inadequate levels of paracrine factors from the cells, which may be due to poor retention of cells due to cell death, removal via immunologic mechanisms, and simple "washout" following delivery, leaving cells with only a brief opportunity to exert beneficial effects. Embodiments of the implantable bioreactor disclosed herein can solve the problems of diffusion or washout by providing adequate, prolonged delivery of paracrine factors secreted from the bioreactor while protecting the contents of the bioreactor from immunologic clearance in an enclosed housing. The disclosure includes in one embodiment, a minimally invasive percutaneous bioreactor and, in another embodiment, an implantable device either of which can adequately produce and release paracrine factors. The bioreactor can also be used to promote healing and regeneration by release of paracrine factors in any other tissue or organ.

As used herein, "bioreactor" refers to a collection of cells, in a housing, capable of producing and releasing paracrine factors. As used herein, "paracrine factors" are diffusible components produced by one cell to affect another cell. The diffusible components can be any protein, growth factor, biomolecule, nutrient or fluid produced by the cells housed in the bioreactor. As used herein, "cells" include any cell capable of producing and releasing paracrine factors. As used herein, "cells" can include pancreatic beta cells, endothelial cells, myocardial cells, and fibroblasts, as well as genetically altered cells. As used herein, "stem cells" include, but are not limited to, embryonic and adult stem cells. Embryonic stem cells include, without limitation, totipotent, pluripotent and multipotent stem cells, and adult stem cells include, without limitation, mesenchymal stem cells, adipose-derived stem cells, whole bone-marrow derived stem cells and endothelial progenitor stem cells. Combinations of stem cells and these other cell types are also contemplated.

Various embodiments of the disclosure include (a) an implantable bioreactor which enhances recovery of injured myocardium and other tissue utilizing a stem cell strategy; (b) a percutaneously implantable bioreactor, which also includes an easily retrievable percutaneous bioreactor allowing removal once an intended treatment period is complete; (c) a temporary implantable device that releases paracrine factors, which are generated de novo by stem cells and/or other cell types; (d) a permanent implantable device that releases paracrine factors, which are generated de novo by stem cells and/or other cell types; (e) a bioreactor implanted via a standard vascular sheath; (f) an implantable bioreactor which locally releases paracrine factors in the target tissue; (g) an implantable bioreactor which contains a barrier with pores which allow the release of cell-derived biomolecules, but not large enough to allow the entry of immunologic and other cells, or the egress of the stem cells and/or other cell types; (h) an implantable bioreactor which contains a barrier composed of the material described herein and which is designed to allow the release of cell-derived biomolecules, but not large enough to allow the entry of immunologic and other cells, or the egress of the stem cells and/or other cell types; and (i) an implantable bioreactor which systemically releases paracrine factors.

Disclosed herein are two classes of implantable bioreactors. Class I includes bioreactors designed for systemic delivery of produced bio-products. Class II includes bioreactors designed for local delivery of produced bio-products at the target tissue. Both classes encompass embodiments for implantation via open surgery, percutaneous techniques, or any other technique to effect implantation. Both classes, in various embodiments, can adhere to a medical device.

Class I implantable bioreactor for systemic delivery. In one embodiment, the systemic delivery implantable bioreactor comprises an enclosure housing stem cells and/or other cell types which produce and release paracrine factors. The enclosure comprises, in one embodiment, a physical enclosure fabricated with a semi-porous membrane, or in another embodiment fabricated with a microporous polymer matrix encapsulating the cells. The enclosure includes micropores impermeable to cells, but of sufficient size to allow free permeation of fluid so that biomolecules, waste and nutrients can be transferred efficiently and without hindrance. In one embodiment, the implantable bioreactor is deployed in the intravascular space (such as central veins and large arteries), but implantation into any other body cavity, tissue, blood vessel, or organ is also contemplated. In one embodiment, the implantable bioreactor is temporarily implanted and retrieved later. In another embodiment, the implantable bioreactor remains indefinitely as a permanent implant.

Figure 2:
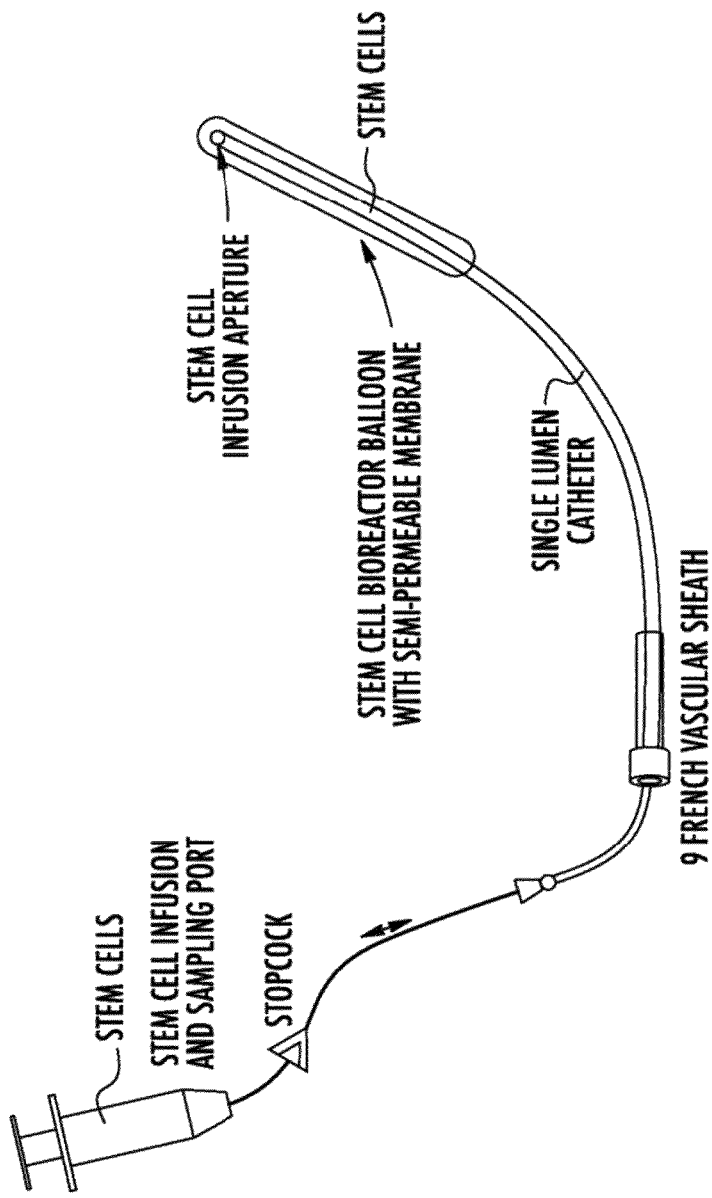
FIG. 2: Simplified catheter-based temporary stem cell bioreactor.

In another embodiment of a systemic delivery bioreactor, the implantable bioreactor comprises a membranous pouch which contains within its lumen stem cells and other cell types and/or media to enhance the viability of the stem cells and which is constructed of a semi-permeable membrane which shields the cells from immunologic attack and allows the release of the paracrine factors and other biomolecules. Optionally, the membranous pouch can be designed to permit the release of the cells. In various embodiments, the membranous pouch can be (a) stand-alone, in which case it can be surgically implanted, or (b) mounted on a wire or catheter, in which case it can be percutaneously implanted, or (c) mounted as part of another implantable device, in which case it can be implanted along with the other device. In an embodiment, the membranous pouch can be pre-filled with its intended contents or, if attached to a catheter, filled and potentially emptied and re-filled during and after implantation. When percutaneously implanted, the device can be passed via a vascular sheath (as illustrated in FIG. 2).

Stand-alone Membranous Pouch-based Bioreactor. In an embodiment, the bioreactor is a stand-alone membranous pouch designed to be surgically implanted. Material composition: The pouch housing is made of a semi-permeable membrane with a pre-defined molecular weight cut-off designed to effectively restrict movement of cells, but allow free transfer of paracrine factors, nutrients, and waste. The membrane can be composed of a wide spectrum of cellulosic (such as cellulose acetate) and synthetic materials (such as polysulfone, polyamide, polyacrylonitrile, and their copolymers, polymethylmethacrylate, polytetrafluroethylene and their various derivatives, silicon carbide, and micro-machined porous silicon diaphragms, among others). Coatings: As long as membrane porosity is not disturbed, the interior surface of the pouch can be coated with molecules which enhance stem cell attachment and function. The exterior of the pouch can be coated with anticoagulants to minimize thrombosis, and/or other substances to improve deliverability. This adjustment of coatings is well known to those of ordinary skill in the art. Geometry: The physical shape of the pouch can be designed to incorporate surface undulations and crevices to maximize surface area for mass transfer. Bioreactor contents: Any number of stem cells and/or other cell types or cells with and/or without genetic alterations can be used in the device based, in part, on the type of injury and organ that is being targeted for regeneration. The cells can be used stand-alone or bathed in a media containing any number of proteins, growth factors, or other molecules.

Figure 3:
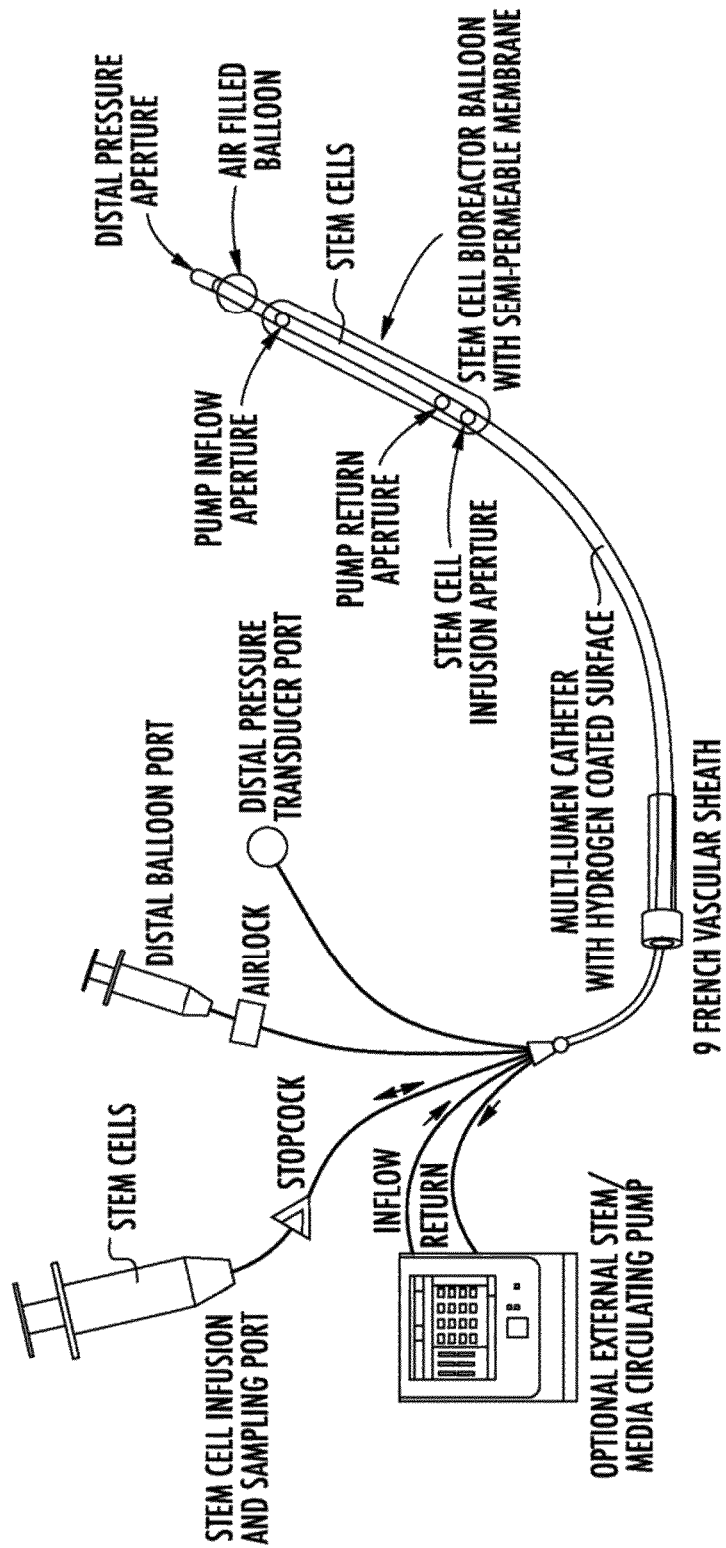
FIG. 3: Catheter-based temporary stem cell bioreactor.

Catheter-mounted Membranous Pouch-based Bioreactor. In an embodiment the bioreactor is a pouch bioreactor, as described above, which is attached to catheter tubing with ports connecting the pouch lumen to the catheter exterior, allowing infusion, sampling, and circulation of cells and media. In another embodiment, multiple lumens within the housing of the catheter can provide additional options for continuous circulation of stem cells within the pouch, and an open distal port can be used as an intravenous line or for central venous pressure measurement (as illustrated in FIG. 3). Alternatively, the pouch bioreactor can be mounted directly on a wire.

The catheter housing can made of polyvinyl chloride tubing (or any other suitable biocompatible material) composed of a multitude of lumens, proximal access ports and distal apertures, similar to standard multi-lumen central venous catheters. These ports can be used for removal and/or replacement of cells, media, or other substances which may promote maintenance of the cells and/or enhance their function. Coatings: The surface of the catheter upon which the bioreactor is mounted and the portion of which is inside of the bioreactor can be coated with molecules which enhance stem cell attachment and function. Some of these molecules include polylysine, fibronectin, or other proteins with Arg-Gly-Asp (RGD) sequences. This can be accomplished by first oxidizing the catheter surface in a plasma reactor or with chemical oxidizing agents such as potassium permanganate, then reacting the surface with the appropriate molecular functional group. The exterior of the catheter can also be spray- or dip-coated with an anti-coagulant (such as heparin) to minimize thrombus formation during and following implantation. Air-filled guiding balloon: A small balloon (~1 cm in diameter) can be placed near the tip of the catheter, which upon filling with air, can assist in guiding intravascular placement. Guidewire directability is provided by incorporation of a channel for the introduction of a steerable and removable guidewire within the device. Bioreactor contents: Any number of stem cells and/or other cell types or cells with and/or without genetic alterations can be used in the device based on the type of injury and organ that is being targeted for regeneration. The cells could be used stand-alone or bathed in a media containing any number of proteins, growth factors, or other molecules. The device would also allow for slow infusion, intermittent recycling or continuous circulation of cells, cell-conditioned media, concentrated paracrine factors, or any other fluids that are determined to have a beneficial effect. Removability: The catheter-based device can be easily removed when desired. The pouch housing is first evacuated by withdrawing its contents through the infusion port. Vacuum is then created allowing the pouch to collapse to a small profile facilitating removal. The entire device can then be pulled out of the body. The vascular sheath is removed and manual compression or vascular closure devices, if needed, can be used to achieve hemostasis.

Secondary Device-mounted Pouch-based Bioreactor. In an embodiment, pouch bioreactors as described above can be attached to various other secondary devices and implanted with the device. The pouch bioreactors can be miniaturized as needed to attach to the secondary device. In the cardiovascular arena, secondary devices include, but are not limited to, stents, intra-aortic balloon pumps, percutaneous and surgically implanted ventricular assist devices, percutaneous and surgically implanted prosthetic valves and valve clips or rings, endovascular grafts, thrombus filters, pacemaker or defibrillator surfaces or leads, septal occluders, atrial appendage closure devices, pulmonary artery catheters, venous catheters, and arterial catheters, among others. Outside the cardiovascular arena, any implantable device conferring access to a target tissue is a possible candidate for attaching a pouch-based bioreactor. These variations are evident to one of ordinary skill in the art.

Encapsulant-based Cell Enclosure. In an embodiment, an implantable encapsulant-based bioreactor consists of a matrix encapsulating desired cells and media coated on a surface. The matrix can be (a) coated directly to a tissue surface or (b) coated on a separate implantable device. The matrix can be pre-formed and stored for later use, or stored in its individual component reactants and then prepared on site when needed. The matrix can be composed of a number of polymers including but not limited to polyethylene glycol (PEG), hyaluronic acid, chitosan, dextran, collagen or self-assembling oligopeptides. Factors such as the arginine-glycine-aspartic acid (RGD) oligopeptide can also be incorporated within the matrix to assist in stem cell adhesion and enhance proliferation and function. The matrix used will be porous enough to allow free transfer of growth factors, nutrients and wastes, while restricting mobility of stem cells. At its lower dimensional limit, single cells can be encapsulated using this method. For example, a hydrogel matrix, which is typically 90% water, is porous enough to allow free transfer of growth factors and other substances, yet will restrict mobility of stem cells. Also arising from the high water content are the excellent anti-fouling properties of the free surface.

Direct Tissue Coating. In an embodiment, matrices encapsulating desired cells and media are directly coated onto a tissue surface. This can be performed via either direct surgical exposure of the target tissue, or through percutaneous injection into the target tissue or into a surface or potential space (e.g., pericardial sac, peritoneal space) around the target tissue.

Coating onto an Implantable Device. In an embodiment, matrices encapsulating desired cells and media are applied to a secondary implantable device. Application of the matrix to the device can be via dip-coating, spray-coating, spin-coating, or any other method that achieves adequate adhesion of the matrix to the implantable device. Coating may be performed long a priori or immediately before device implantation. In the cardiovascular arena, possible secondary implantable devices include, but are not limited to the pouch-based bioreactor, a microfabricated cellular enclosure, stents, intra-aortic balloon pumps, percutaneous and surgically implanted ventricular assist devices, percutaneous and surgically implanted prosthetic valves and valve clips or rings, endovascular grafts, thrombus filters, pacemaker or defibrillator surfaces or leads, septal occluders, atrial appendage closure devices, pulmonary artery catheters, venous catheters, and arterial catheters, among others. Outside the cardiovascular arena, any implantable device conferring access to a target tissue is a possible candidate for coating with the matrices.

Class II Implantable Bioreactor for Local Delivery. Local delivery of paracrine factors confers dual advantages of direct targeting of diseased tissue and reduction or prevention of any systemic side effects. In an embodiment, an implanted device is coated with cells using cell-specific ligands or antibodies as cell anchors. In another embodiment, a cell micro-enclosure, constructed using micro-electro-mechanical systems (MEMS) fabrication technology, is disclosed, for implantation in small target tissues, such as the intracoronary space. In another embodiment, miniaturized forms of the bioreactors of Class I can be utilized for local delivery when the bioreactor is deployed at the appropriate target location.

Stand-alone Cell Coated Device. Any implantable device (including any of the embodiments described herein) can be coated with a monolayer of a desired cell type possibly involving the use of cell-specific ligands or antibodies as anchors. For stem cells, anchoring ligands and antibodies include, but are not limited to RGD oligopeptides and those oligopeptides containing the sequence Ile-Lys-Val-Ala-Val, as well as anti-CD34, and anti-CD31. The coated device can be prepared prior to implantation by immersing it in a solution containing the appropriate cell type. In addition, native cells may attach after implantation. For instance, if the goal is myocardial healing and regeneration post infarction, an intracoronary stent could be coated with stem cell-specific ligands and antibodies and then immersed in a solution containing stem cells before coronary implantation.

Cell Coat and Overcoat. A variation of this embodiment for cells susceptible to immunologic attack would be to bind the cells to the desired surfaces using appropriate ligands/antibodies as described above and, in addition, layer above these cells an overcoat of a semi-permeable matrix or a semi-permeable membrane. The semi-permeable matrix or membrane would confer immunologic isolation while allowing free permeation of bio-molecules, fluids, nutrients, and waste.

Microfabricated Cellular Micro-enclosure. Cell micro-enclosures of specific dimensions, pre-determined porosity and pore patterns can be fabricated using microfabrication technology. These microenclosures can be constructed to be far smaller and with far more precise pore characteristics than available semi-permeable membranes. The pores can be designed to be impermeable to cells, yet freely permeable to fluid, nutrients, paracrine factors and/or other bio-products, wastes and nutrients. The enclosures can be coated with cell-specific ligands, antibodies or other factors which are well known to those of ordinary skill in the art to facilitate cell adhesion and proliferation. The enclosures can be used stand-alone or attached to a separate implantable device. In one embodiment, the micro-enclosures are filled with stem cells and/or other cells and are bonded to a coronary stent for myocardial healing and regeneration after infarction.

Figure 4:
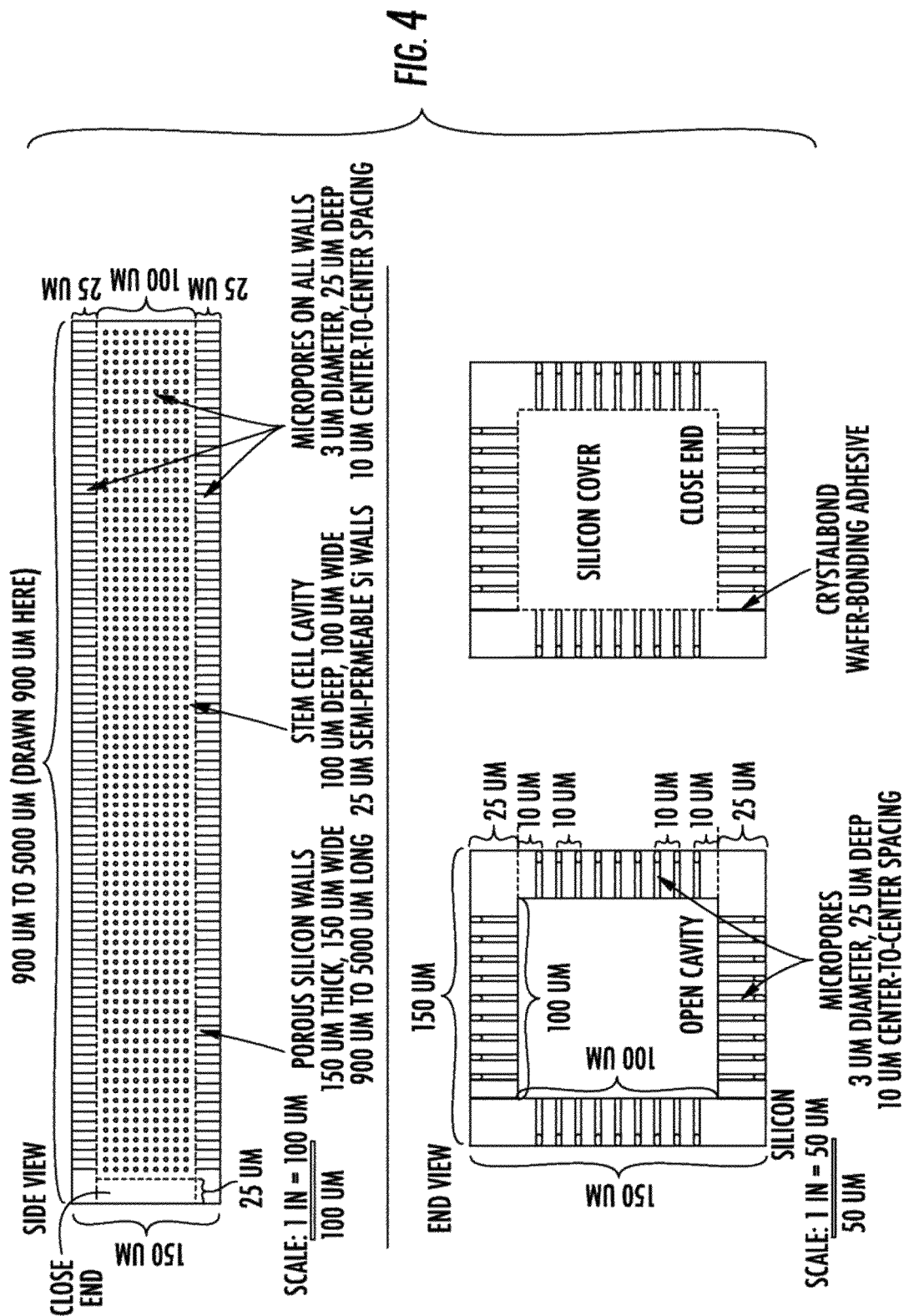
FIG. 4: Microporous silicon cell micro-enclosure.
Figure 5:
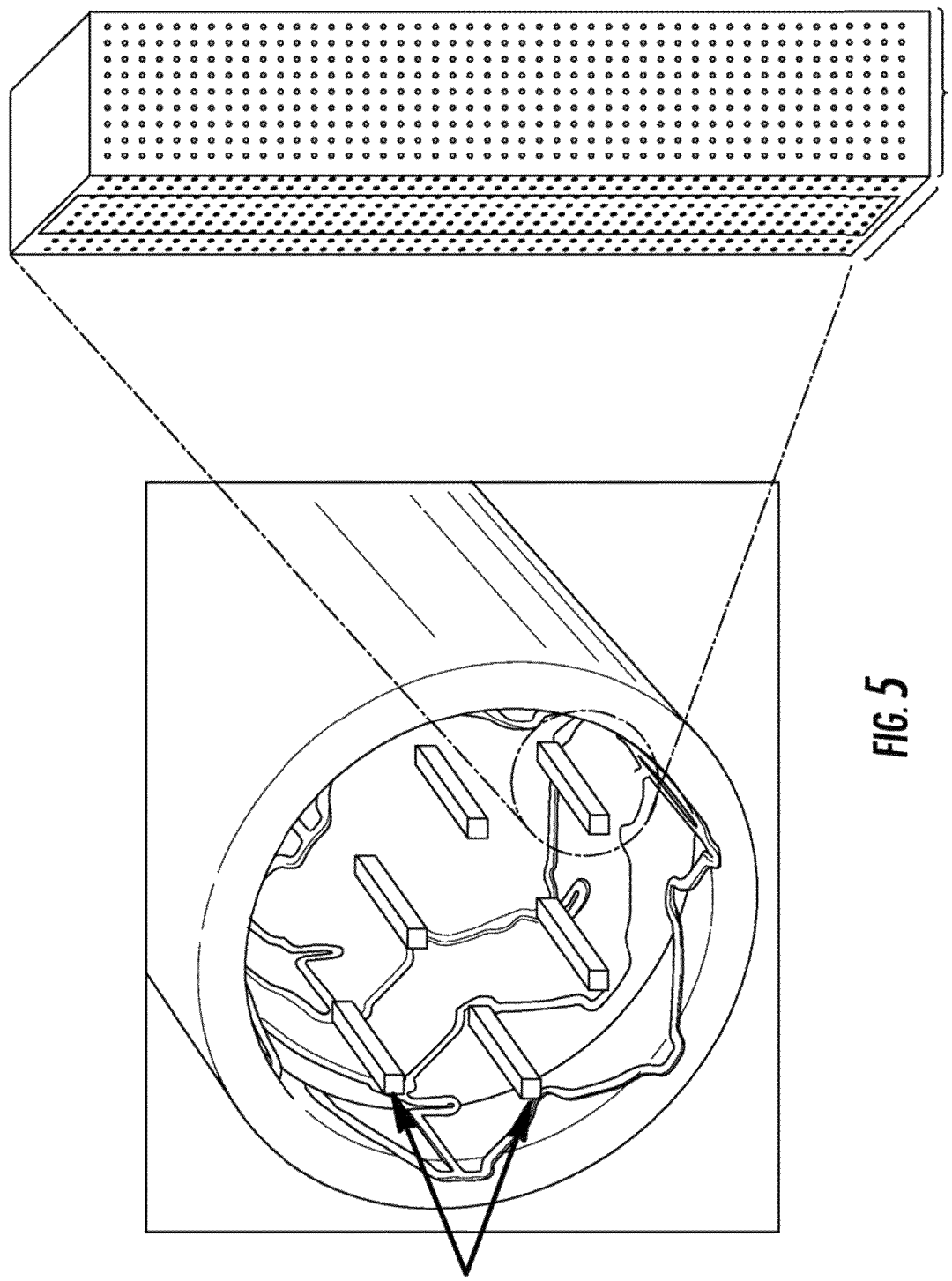
FIG. 5: Cellular micro-enclosure mounted to a vascular stent.
Figure 6:
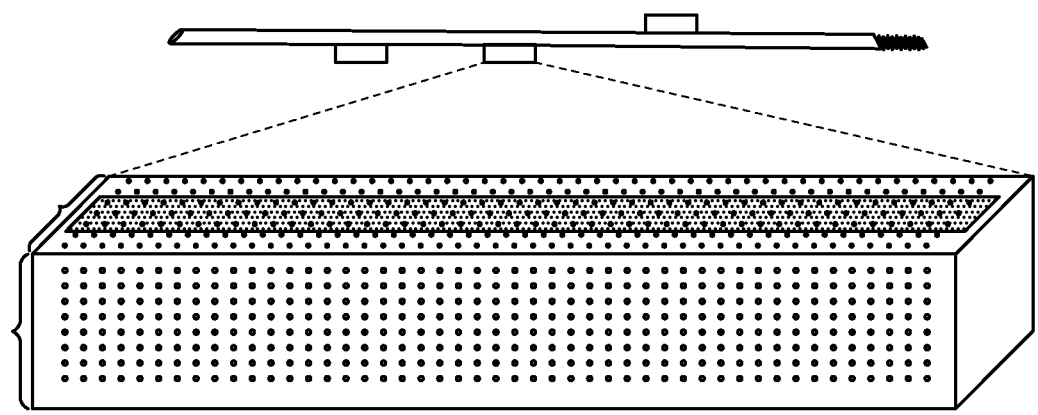
FIG. 6: Microfabricated cellular micro-enclosure bonded to coronary guide wire.
Figure 7:
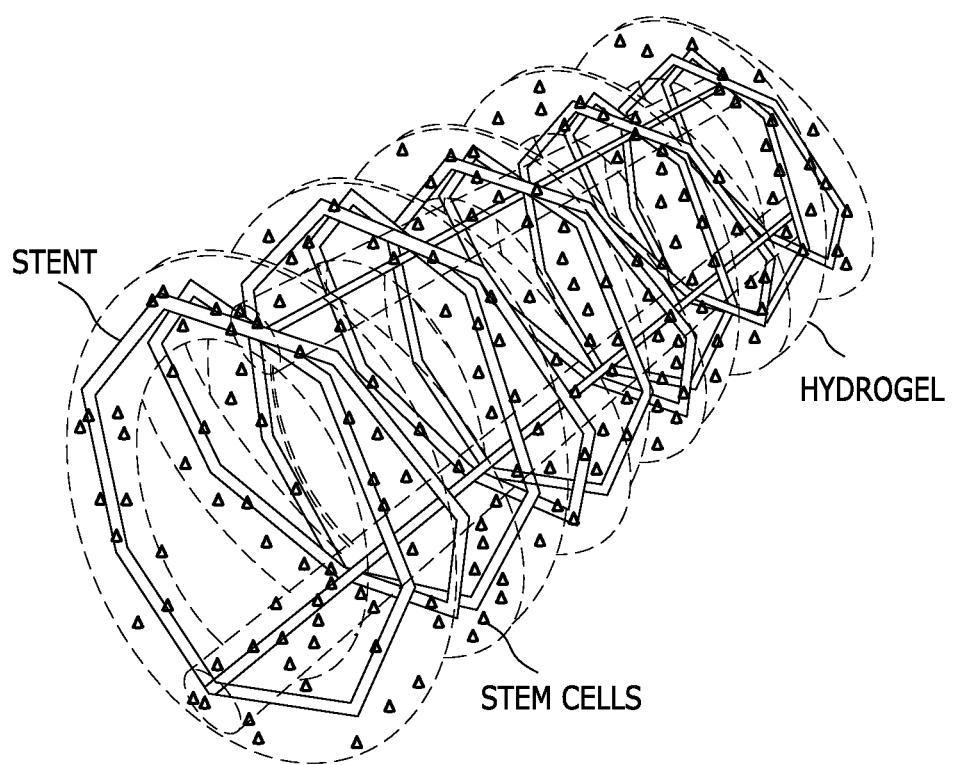
FIG. 7: Hydrogel coated stent encapsulating stem cells within a crosslinked hydrophilic polymer.

In one embodiment, microporous cellular enclosures can be fabricated from silicon wafers. Using photolithographic techniques, multiple pores of specific diameters (e.g. 0.1 um to 15 μm) can be etched into the device layer of a silicon-on-insulator (SOI) wafer. This is followed by creating cell cavities by etching multiple large trenches into the handle wafer side. The handle wafer trenches can be positioned directly beneath the device layer pores using backside alignment. The buried oxide between the two silicon surfaces can then be removed, releasing the silicon semi-permeable membrane. The micro-enclosure can then be coated with cell specific ligands and antibodies. Finally, stem cells and/or other cell types, drug, and growth media can then be placed in the trenches before sealing the cavity. Repeated iterations of this process can yield porous silicon micro-enclosures (as illustrated in FIG. 4) that can then be bonded to a coronary stent.

Miniaturized Bioreactors. The implantable bioreactors described herein can all be used for local delivery with appropriate miniaturization and placement. Pouch-based enclosures could be miniaturized through micromachining. Thin, uniform coatings of the matrix-encapsulated cells could be produced using spray-coating or spin-coating. In another variation, direct micro-injection of matrix-encapsulated cells into target diseased tissue can be used as a strategy for local delivery.

EXAMPLES

The examples presented herein illustrate, but are not intended to limit, the scope of protection being sought.

Example 1: Stem Cell Viability and Paracrine Factor Release from Miniature Bioreactors In Vitro Methods. To determine whether stem cells can survive in, and produce and release paracrine factors from the cellulose acetate semi-permeable membrane used in the implantable pouch-type bioreactor prototype, we devised an experimental model using miniature versions of the device chamber. In this model, short segments of the semi-permeable membrane with $10^6$ Da pores were fashioned into tubes, and the ends secured with sterile suture; in addition, limited experiments have been performed to date using $10^5$ Da pore membrane. One million human mesenchymal stem cells (MSCs) or bone marrow mononuclear cells (BMMNCs) were injected into the lumen of the chamber, and then the entire device was submerged in cell culture media for incubation (see FIG. 1). Samples of the media outside the device were taken at 24 hrs, 72 hrs, and 7 days for the $10^6$ Da experiments. All samples underwent measurement of 8 different paracrine factors (PFs) by Quansys Q-Plex Human Angiogenesis Array (n=3-6). This micro-array can simultaneously assess for the presence and quantity of: Vascular Endothelial Growth Factor (VEGF), Hepatocyte Growth Factor (HGF), Basic Fibroblast Growth Factor (bFGF), Interleukin-8 (IL-8), Tissue Metalloproteinase Inhibitors 1 and 2, Platelet-Derived Growth Factor-BB (PDGF-BB), and Tissue Necrosis Factor Alpha (TNF-α). Multiple 1 mL aliquots of the conditioned media were collected at stored at −80° C. until the time of analysis. Results of media collected from mini-bioreactors containing stem cells were compared to those from mini-bioreactors not containing stem cells media as controls. In addition, at each time point bioreactors were opened and cells within were removed for cell viability assessment using trypan blue exclusion (n=3).

Results: Paracrine Factor Production.

Samples of cell culture media collected from outside of $10^6$ Da mini-bioreactors containing MSCs showed substantial production of VEGF, HGF, IL-8, TIMP-1, and TIMP-2 that increased with time. Production of bFGF was detected at 24 h, but decreased over time. The remaining factors, PDGF-BB, and TNF-α were not detected.

Conditioned media samples taken from outside mini-bioreactors containing BMMNCs showed production and release of relevant paracrine factors as well, but in a pattern different from that of the MSCs. BMMNCs showed increasing production of IL-8, TIMP-1, and TIMP-2 over time, with production of IL-8 substantially greater than that of the MSCs. TNF-α was detected as well, though decreased over time. The factors VEGF, HGF, bFGF, and PDGF-BB were not detected (see Table below) in conditioned media taken from experiments using BMMNCs.

TABLE

Stem Cell Viability and Paracrine Factor Production from Miniature Bioreactors made using $10^6$ Da Cellulose Acetate Semi-Permeable Membrane.

| | | | | Average Analyte Concentration Mean (pg/mL) | | | | | | | |
|---|---|---|---|---|---|---|---|---|---|---|---|
| Cell Type | t | n | Viability | VEGF | HGF | bFGF | IL-8 | PDGF-BB | TIMP-1 | TIMP-2 | TNFα |
| MSCs | 24 h | 6 | 89.4% | 112.6 | 0.0 | 60.9 | 8.6 | 0.0 | 7903.2 | 2118.5 | 0.0 |
| | SD | | | 6.3 | 0.0 | 6.3 | 3.0 | 0.0 | 8818.0 | 595.7 | 0.0 |
| | 72 h | 6 | 79.1% | 236.5 | 112.1 | 31.5 | 18.2 | 0.0 | 3339.3 | 7799.2 | 0.0 |
| | SD | | | 57.7 | 25.2 | 5.3 | 4.2 | 0.0 | 587.7 | 2191.3 | 0.0 |
| | 7 d | 6 | 75.4% | 676.4 | 348.0 | 29.5 | 97.5 | 0.0 | 89544.8 | 8165.1 | 0.0 |
| | SD | | | 81.2 | 61.5 | 5.2 | 87.5 | 0.0 | 133399.1 | 2245.8 | 0.0 |

TABLE-continued

Stem Cell Viability and Paracrine Factor Production from Miniature Bioreactors made using 10⁶ Da Cellulose Acetate Semi-Permeable Membrane.

| | | | | Average Analyte Concentration Mean (pg/mL) | | | | | | | |
|---|---|---|---|---|---|---|---|---|---|---|---|
| Cell Type | t | n | Viability | VEGF | HGF | bFGF | IL-8 | PDGF-BB | TIMP-1 | TIMP-2 | TNFα |
| Control (no cells) | 24 h | 3 | n/a | 0.0 | 0.0 | 0.0 | 0.0 | 0.0 | 0.0 | 0.0 | 0.0 |
| | SD | | | 0.0 | 0.0 | 0.0 | 0.0 | 0.0 | 0.0 | 0.0 | 0.0 |
| | 72 h | 3 | n/a | 0.0 | 0.0 | 0.0 | 0.0 | 0.0 | 0.0 | 0.0 | 0.0 |
| | SD | | | 0.0 | 0.0 | 0.0 | 0.0 | 0.0 | 0.0 | 0.0 | 0.0 |
| | 7 d | 3 | n/a | 0.0 | 0.0 | 0.0 | 0.0 | 0.0 | 0.0 | 0.0 | 0.0 |
| | SD | | | 0.0 | 0.0 | 0.0 | 0.0 | 0.0 | 0.0 | 0.0 | 0.0 |
| BMMNCs | 24 h | 6 | 78.4% | 0.0 | 0.0 | 0.0 | 1497.7 | 0.0 | 327.3 | 0.0 | 76.9 |
| | SD | | | 0.0 | 0.0 | 0.0 | 637.0 | 0.0 | 40.6 | 0.0 | 41.3 |
| | 72 h | 6 | 64.2% | 0.0 | 0.0 | 0.0 | 4418.5 | 0.0 | 1063.1 | 84.8 | 49.2 |
| | SD | | | 0.0 | 0.0 | 0.0 | 2712.4 | 0.0 | 296.6 | 10.6 | 13.4 |
| | 7 d | 3 | 61.5% | 0.0 | 0.0 | 0.0 | 6855.7 | 0.0 | 1927.9 | 447.5 | 23.7 |
| | SD | | | 0.0 | 0.0 | 0.0 | 647.5 | 0.0 | 201.3 | 79.1 | 2.5 |
| Control (no cells) | 24 h | 3 | n/a | 0.0 | 0.0 | 0.0 | 0.0 | 0.0 | 0.0 | 0.0 | 0.0 |
| | SD | | | 0.0 | 0.0 | 0.0 | 0.0 | 0.0 | 0.0 | 0.0 | 0.0 |
| | 72 h | 3 | n/a | 0.0 | 0.0 | 0.0 | 0.0 | 0.0 | 0.0 | 0.0 | 0.0 |
| | SD | | | 0.0 | 0.0 | 0.0 | 0.0 | 0.0 | 0.0 | 0.0 | 0.0 |
| | 7 d | 3 | n/a | 0.0 | 0.0 | 0.0 | 0.0 | 0.0 | 0.0 | 0.0 | 0.0 |
| | SD | | | 0.0 | 0.0 | 0.0 | 0.0 | 0.0 | 0.0 | 0.0 | 0.0 |

Stem Cell Viability.

Assessment of MSC and BMMNC viability in mini-bioreactors made of $10^6$ Da cellulose acetate membrane at 24 h, 72 h, and 7 d showed substantial cell viability with 89.4%, 79.1%, and 75.4% for MSCs, respectively, and 78.4%, 64.2%, and 61.5% for BMMNCs (see Table above).

Summary. These experiments demonstrate that two types of stem cells, MSCs and BMMNCs, survive for up to seven days in culture in miniature bioreactor chambers made of the same $10^6$ Da cellulose acetate membrane used for the catheter-based implantable bioreactor prototype, and that during this time release paracrine factors (PFs) relevant to angiogenesis and tissue repair. The amount and type of PFs released by MSCs differ from those of BMMNCs. It is yet unclear whether this represents an intrinsic difference in the cell types, or a differential response to growth within the cellulose acetate membrane. Overall, these results suggest that the $10^6$ Da cellulose acetate semi-permeable membrane is compatible with MSC and BMMNC cell survival and PF release, though there are differences in the combination of PFs released by the different cell types.

Example 2: Implantation of Bioreactor Prototype in Farm Pig

Methods. Bioreactor prototype devices were implanted in two farm pigs (~25 kg). Each device was fashioned from $10^6$ Da cellulose acetate semi-permeable membrane secured to an 8 F clinical grade multi-lumen catheter. In both cases a surgical cut-down procedure was performed over the right neck to expose the external jugular vein (EJ) after initiation of general anesthesia and endotracheal intubation. Using fluoroscopic guidance, a 14 F vascular sheath was inserted in the EJ over the wire. The bioreactor device prototype was then passed through the sheath and advanced to the junction of the superior vena cava (SVC) and right atrium (RA). In the first experiment the device was left in place for 1 hour, after which a suspension of $2.5 \times 10^6$ human MSCs was injected into the device. The device was then left in place for another 90 minutes, during which continuous ECG monitoring and intermittent fluoroscopic venography were performed, the latter to determine whether there was any impediment to blood return to the heart via the EJ/SVC. The device was then removed and inspected and the animal euthanized using potassium chloride infusion.

In the second experiment the bioreactor prototype was again advanced to the SVC-RA junction, and a suspension of $2 \times 10^6$ human MSCs were infused into the bioreactor chamber via the catheter lumen. The bioreactor and vascular sheath were then sutured in place and the surgical wound closed. The animal was then allowed to awaken and the device was maintained in place for 24 hours. The animal was then returned to the surgical suite and general anesthesia induced. Fluoroscopic venography was performed as previously and the device removed for inspection. The animal was then euthanized as above.

Results. In both experiments, the prototype bioreactor was well tolerated with no evidence of vascular, hemodynamic, or arrhythmic compromise. Fluoroscopic venography showed no evidence of vascular compromise or intra-vascular thrombus formation during either the 2.5 hours the device was in place during the first experiment, or after 24 hours in the second experiment. In the second experiment small amounts of thrombus were found at both ends of the bioreactor lumen, where the cellulose acetate membrane was secured to the catheter shaft, but none on the membrane itself. The addition of MSCs to the bioreactor lumen did not appear to affect biocompatibility of the device.

Summary. These preliminary results suggest that the prototype bioreactor device is well tolerated in vivo for up to 24 hours with no evidence of vascular, hemodynamic, or arrhythmic compromise. The presence of a small amount of thrombus at the attachment points of the bioreactor chamber to the vascular catheter indicates the need for further optimization; however, the cellulose acetate membrane itself appears biocompatible.

Example 3: Hydrogel for Stem Cell Encapsulation and Intravascular Deployment Hydrogel Crosslink Chemistry. We describe a method for immobilizing stem cells on the surfaces of an implantable stent using a biologically inert hydrogel coating. Polyethylene glycol (PEG) was chosen to encapsulate the stem cells because of its biocompatibility, antifouling properties, and permeability to biomolecules. It is a neutral, water-soluble polymer that forms hydrogels when crosslinked in the presence of water. Crosslinks form in our proprietary system through the reaction between N-hydroxysuccinimide (NHS)-activated esters and amine groups. The two functional groups react to form an amide bond with the loss of the NHS group. The reaction rate is greatest at a pH between 7 and 10 and is much slower at a pH below 6. This difference in reaction rates allows for convenient handling of the liquid hydrogel precursor at pH of 6, while raising the pH slightly to physiologic pH (7.4) results in immediate solidification. To form a fully crosslinked gel, we mix a PEG molecule with two or more activated ester groups (NETS-PEG) and a PEG molecule with 2 or more amine groups (amine-PEG) to generate a 3-dimensional hydrogel polymer network. The higher the average functionality, the more rapidly a gel forms for any given number of crosslinks. A hydrogel is formed by mixing an 8-arm polyethylene glycol molecule with 8 NETS-activated esters with a diamine-functionalized polyethylene glycol. The average functionality of 5 for this system is chosen to efficiently generate fully crosslinked gels.

Figure 8:
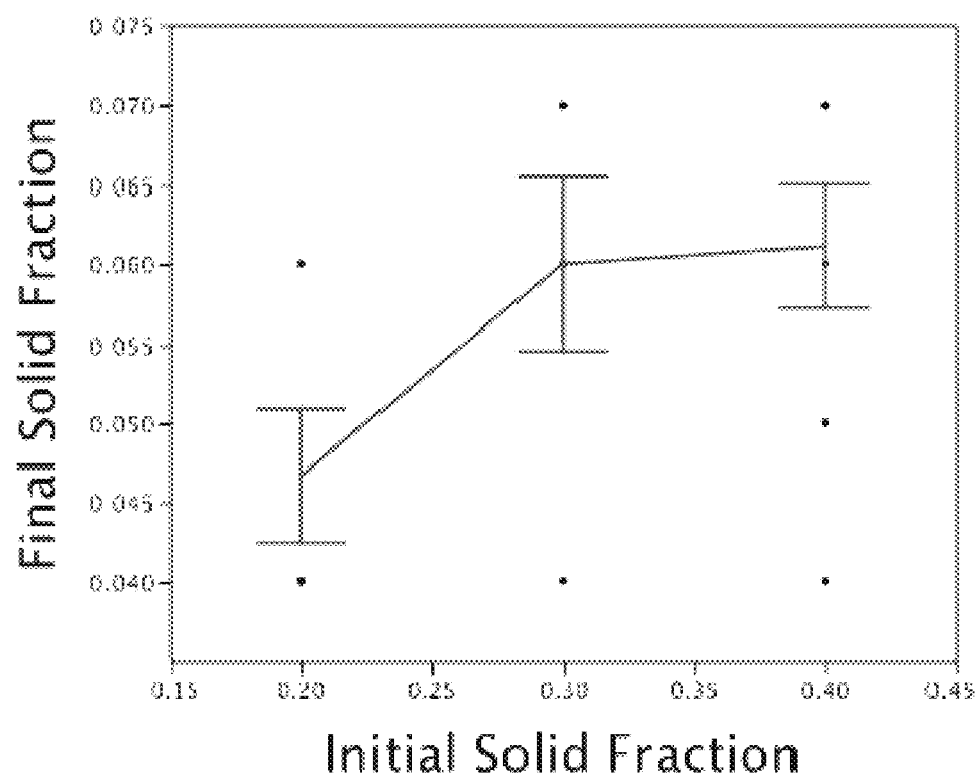
FIG. 8: Final solid fraction of the hydrogel plotted versus the initial solid fraction. Higher final solid fractions are associated with greater crosslink densities.
Figure 9:
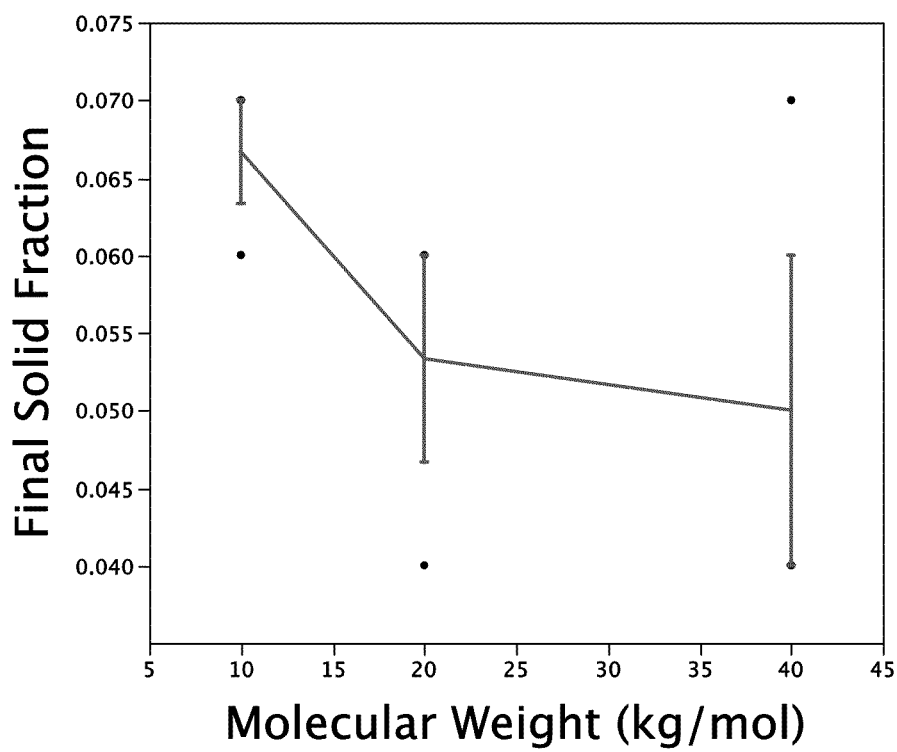
FIG. 9: Final organic solid fraction plotted against the molecular weight of the polyethylene glycol precursor.

Polymer Precursor Concentration. The hydrogels initially contain between 5% and 50% organic solids by weight, with water constituting the remainder. After the gel is formed, it expands to many times its own weight, typically 4×-5×, by soaking up additional water. Water will continue to absorb until the gel reaches equilibrium, which is usually around 5%-10% organic solids by weight. For this system, higher initial solid fractions facilitate more efficient crosslinking reactions between the NETS-PEG and diamine-PEG. The greater reaction efficiency can be seen by the finding that a higher initial solid fraction results in a higher final solid fraction (FIG. 8). As will be described below, denser, less swollen films have a higher crosslink density.

Hydrogel Crosslink Density. Generally speaking, the equilibrium fraction of organic solids in a hydrogel ($\upsilon_p$) increases with increasing crosslink density ($\rho_x$, crosslinks per volume, given in mol/L), and decreases with the molecular weight of the polyethylene glycol between crosslinks ($M_c$).

$$\rho_x = -\frac{1}{\bar{v}}\left(\frac{\ln(1-\upsilon_p)+\upsilon_p+\chi\upsilon_p^2}{\upsilon_p^{1/3}-\upsilon_p/2}\right)$$

where $\bar{v}$ is the molar volume of water and $\chi$ is the Flory-Huggins chi parameter.

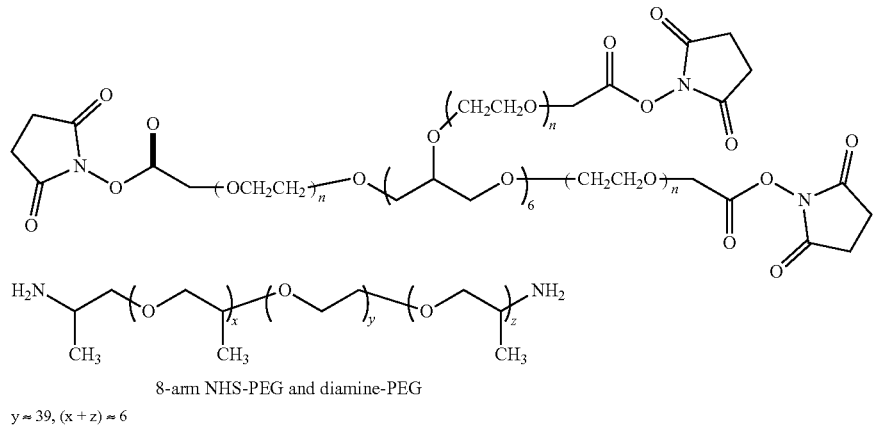

8-arm NHS-PEG and diamine-PEG
y ≈ 39, (x + z) ≈ 6

This NHS ester/amine reaction was chosen for its low toxicity, biocompatibility, and the convenience of triggering the reaction using a mild pH change. Other polyethylene glycol hydrogels are more commonly formed by a photoinitiated radical polymerization. Although stem cells have been shown to survive photopolymerization, the procedure employs UV light to generate free radicals, both of which are usually used to sterilize samples, and hence may harm the stem cells.

Note that other polymerization chemistries are possible, such as isocyanate/amine, epoxy/amine, isothiocyanate/amine, alcohol/glutamate, and thiol/maleimide. Although most of these reaction chemistries may be used in lieu of the current NETS ester/amine reaction, many have higher toxicity, sub-optimal reaction kinetics, and do not have the advantage of being able to "switch" on and off with such a mild pH change.

$$\rho_x = \frac{2}{f_{av}}\frac{\rho}{M_c}$$

where $f_{av}$ is the average functionality of the monomers, and $\rho$ is the density. The same phenomenon is observed for proprietary gels.

The molecular weight of the polymer precursor is typically chosen to control the crosslink density. Typical values range from 1000 g/mol to 100,000 g/mol. Note that high molecular weight leads to lower crosslink densities and lower stiffness. The other mitigating factor is the reaction conversion. Low conversions decrease the crosslink density, increase the effective molecular weight between crosslinks, and decrease the elastic modulus.

Cell Adhesion. To improve cell viability, it is desirable to allow cells to adhere to the hydrogel and pull themselves into a state of tension. Viability frequently correlates with the lens-like shape the cells take when they successfully form focal adhesion sites with the surrounding matrix whereas a lack of adhesion is characterized by a spherical cell morphology and generally leads to apoptosis. For our proprietary recipe, the addition of RGD oligopeptides facilitates the formation of focal adhesion points through the specific interactions between RGD and integrin. Typical concentrations ranging from 1-20 mM are used to promote cell adhesion.

Our formulation uses cyclo (Arg-Gly-Asp-d-Phe-Lys). The additional lysine residue has a free amine group, which reacts with the NETS-PEG to become incorporated into the hydrogel. The cyclic RGD ring is not strictly required, but it confers greater stability and selectivity over linear RGD peptides.

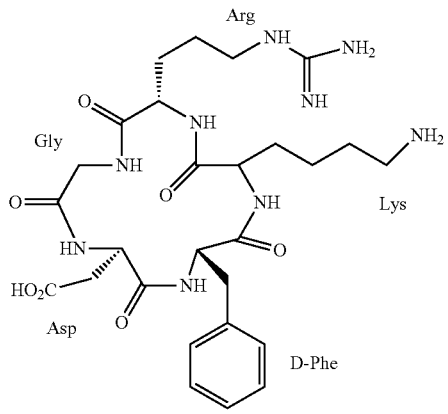 [SMILES: N=C(N)NCCC[C@@H]1NC(=O)C(CCCCN)NC(=O)[C@H](Cc2ccccc2)NC(=O)[C@@H](CC(=O)O)NC(=O)CNC1=O]

Stent Adhesive Layer. The final step is to adjust the pH to a level at which the nucleophilic addition reaction occurs at the fastest rate. NETS-activated PEG tends to lower the pH to a level at which the reaction occurs too slowly, so a small amount of base is typically needed to raise the pH to 7.4, at which the reaction proceeds rapidly to completion.

In our system, we designed an adhesive layer that automatically adjusts the pH from 6 to 7.4. This convenient method makes it possible to prepare the hydrogel precursor and add stem cells and/or other cell types when it is a liquid, and then solidify the gel only after it coats the stent, or another device. The gel precursor solution containing the stem cells and/or other cell types may be painted, sprayed, or dip-coated onto the stent or another secondary device. Gelation typically occurs within ten minutes of coming in contact with the gel precursor solution.

Coating of poly(allylamine) (PAAM) and hexamethylene diisocyanate (HMDI). The adhesive coating is formed by first dipping the stent into a 5% solution of PAAM in water. The stent is then dipped into a 5% solution of HMDI in isopropanol. The HMDI rapidly reacts with the PAAM to form polyurea crosslinks. Since the reaction does not proceed with precise stoichiometry, it will always leave behind a small fraction of amine and isocyanate groups. To ensure that the excess amine groups do not increase the pH too strongly, the coated stent is soaked and rinsed in phosphate buffered saline at a pH of 7.4 until the pH stabilizes at 7.4.

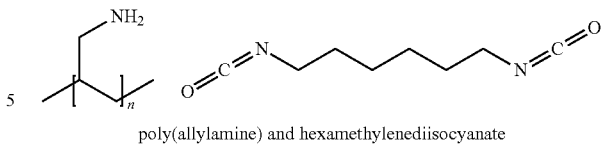
poly(allylamine) and hexamethylenediisocyanate

The excess of basic amine groups in this adhesive coating subsequently increase the pH of the hydrogel precursor solution to initiate the polymerization. These amine groups are free to react with NHS-PEG in the hydrogel precursor solution. HMDI serves a dual function as well: it crosslinks the PAAM by forming polyurea bonds, and any excess isocyanate groups are also free to crosslink with diamine-PEG in the hydrogel precursor solution.

Recipe. To make 200 μL of hydrogel, add 50 mg of N-hydroxysuccinimide-activated polyethylene glycol with 8 activated ester groups (8 arm NETS-PEG, MW=40 kg/mol) to 65 μL of phosphate buffered saline (PBS) at pH 7.4. Stir until dissolved. Excess carboxylic acid groups that are invariably present on the 8 arm NETS-PEG cause the pH to drop to about 6 or lower. Next, add 60 μL of a 10 mg/mL solution of cyclo (arginine-glycine-aspartine-d-phenylalanine-lysine) (RGD-lysine), and 75 μL of a 400 mg/mL solution of polyethylene glycol-diamine (PEG-diamine, MW=2 kg/mol). Finally, the pH is adjusted with sodium hydroxide to 7 to drive the polymerization to completion. Gelation occurs shortly thereafter.

This mixture provides a hydrogel that is roughly 40% solids by weight. It gives an RGD concentration of 5 mM, and uses a 1.5:1 ratio of amine groups to activated esters in order to achieve gelation. Once placed in aqueous buffer solution such as PBS and allowed to equilibrate, the hydrogel absorbs water and swells to give a final composition that is between 5% and 10% solids by weight.

Example 4: Microfabricated Cellular Micro-Enclosures: Detailed Materials & Methods Silicon-on-Insulator (SOI) wafers (4" diameter with a 1-2 micron thick buried silicon oxide layer sandwiched between a 50-micron thick device layer and a 200-250 micron thick handle layer) were cleaned using Piranha solution ($H_2SO_4$/$H_2O_2$) and a de-ionized water rinse and blow dried using nitrogen gas.

The handle layer (which is to contain the cell reservoir) was processed first. The handle layer was patterned using photoresist (AZ9260 to a thickness of 14-15 microns cured at 110° C. for 3 to 4 min) so that the silicon can be etched using a Surface Technology Systems Deep Reactive Ion Etcher (STS DRIE) system. In addition, the surface of the device layer was coated with a 1-2 micron thick layer of photoresist (Shipley 1800 cured at 100° C. for 1 min) to provide added structural strength so that the backside helium flow for the STS DRIE does not cause rupture. Etching was performed completely through the handle layer until the buried oxide layer (BOX) etch-stop was reached. The wafer was then cleaned in acetone at room temperature for 30 to 60 min, sequentially soaked in isopropyl alcohol (IPA) and de-ionized water, and dried in a convection oven at 95° C. for 20 min. The drying process minimized the chances of damaging the fragile device layer.

The device layer (which is to contain the semi-permeable diaphragm) was processed next. The device layer was patterned to specific pore sizes and pore-to-pore dimensions with photoresist (Shipley SC 1800, 2 microns thick, cured at 100° C. for 2 min), taking care to match the photoresist pattern on the device layer with the locations of the cell reservoirs on the handle layer on the back-side. To further structurally protect the device layer in processing, it was mounted to a secondary supporting silicon wafer using liquid CrystalBond spun onto the secondary supporting wafer at 2500 rpm and cured at 100-110° C. for 30-45 sec. After the bonded wafer was allowed to cool to room-temperature, the device wafer layer was etched using the STS DRIE system and intermittently cooled between batches of etching cycles to assure continued structural integrity.

At completion of the device wafer etch, individual cellular micro-enclosures were separated from the wafer. The entire wafer was over-coated with photo-resist (Shipley SC 1800 series) from protection, diced on a diamond saw, and soaked in acetone for 24-48 hours to separate the diced micro-enclosures from the secondary supporting wafer. The individual micro-enclosures were then thoroughly cleaned in repeated washes with heated acetone, isopropyl alcohol and de-ionized water, followed by drying in a convection oven for 15-20 min at 95° C.

Finally, the intermediate buried oxide layer was removed by dipping the micro-enclosures in 49% hydrofluoric acid. Cleaning of the micro-enclosures was then performed in sequential washings in de-ionized water, isopropyl alcohol, followed by final cleaning and sterilization in oxygen plasma using a Trion RIE (Reactive Ion Etcher).

What is claimed is:

1. A method for promoting regeneration of injured myocardium in a subject in need thereof, the method comprising:
    percutaneously delivering a bioreactor to the subject;
    the bioreactor comprising an enclosed housing and paracrine factor producing cells enclosed within the housing;
    the housing being impermeable to the paracrine factor producing cells and impermeable to immunological cells outside of the housing;
    the housing being permeable to growth factors and nutrients, but not the entry of cells, into the housing;
    wherein the housing includes pores sized to allow release of paracrine factors having a molecular weight greater than 500,000 Daltons from the paracrine factor producing cells out of the housing; and
    promoting regeneration of the injured myocardium with paracrine factors produced from the paracrine factor producing cells.

2. The method of claim 1, wherein promoting regeneration of the injured myocardium comprises enhancing recovery of the injured myocardium.

3. The method of claim 1, wherein the bioreactor is delivered into an intravascular space.

4. The method of claim 1, wherein the bioreactor is delivered to the injured myocardium.

5. The method of claim 1, wherein the housing is one of a pouch, a semi-permeable membrane, or a cellular micro-enclosure.

6. The method of claim 1, wherein the housing is expandable and collapsible.

7. The method of claim 1, wherein percutaneously delivering a bioreactor to the subject further comprises:
    introducing the bioreactor into a delivery device; and
    delivering the bioreactor from the delivery device to the injured myocardium or an intravascular space of the subject.

8. The method of claim 7, wherein the housing is a microfabricated cellular enclosure bonded to a coronary stent, and wherein the coronary stent is implanted to permit the transfer of paracrine factors out of the microfabricated cellular enclosure and thereby promote myocardial healing and regeneration after an infarction.

9. The method of claim 1, wherein the paracrine factor producing cells are selected from the group consisting of stem cells, genetically altered cells, endothelial cells and myocardial cells.

10. The method of claim 9, wherein the stem cells are selected from the group consisting of mesenchymal stem cells, myocardial-derived stem cells, and bone marrow mononuclear cells.

11. The method of claim 1, wherein the paracrine factors are selected from the group consisting of vascular endothelial cell growth factor, basic fibroblast growth factor, interleukin-8, tissue metalloproteinase inhibitors 1 and 2, platelet-derived growth factor-BB, tissue necrosis factor alpha, and combinations thereof.

12. A method for promoting regeneration of tissue in a subject, the method comprising:
    percutaneously delivering a bioreactor to the subject;
    the bioreactor comprising an enclosed housing and paracrine factor producing cells enclosed within the housing;
    the housing being impermeable to the paracrine factor producing cells and impermeable to immunological cells outside of the housing;
    the housing being permeable to growth factors and nutrients, but not the entry of cells, into the housing;
    wherein the housing includes pores sized to allow release of paracrine factors having a molecular weight greater than 500,000 Daltons from the paracrine factor producing cells out of the housing; and
    wherein the paracrine factors produced by the paracrine factor producing cells are released out of the housing to promote regeneration of the tissue.

13. The method of claim 12, wherein the housing is one of a pouch, a semi-permeable membrane, or a cellular microenclosure.

14. The method of claim 12, wherein the housing is expandable and collapsible.

15. The method of claim 12, wherein delivering a bioreactor into the subject further comprises:
    introducing the bioreactor into a delivery device; and
    delivering the bioreactor from the delivery device to the tissue or an intravascular space of the subject.

16. The method of claim 15, wherein delivering the bioreactor comprises mounting the bioreactor to a wire or catheter having an infusion port and percutaneously implanting the bioreactor.

17. The method of claim 16, further comprising removing the bioreactor by withdrawing the contents of the bioreactor through the infusion port, applying a vacuum to collapse the bioreactor, and pulling the bioreactor out of the subject.

18. The method of claim 15, wherein delivering the bioreactor comprises mounting the bioreactor onto another implantable device and implanting the bioreactor with the other implantable device.

19. The method of claim 18, wherein the other implantable device is a stent, intra-aortic balloon pump, ventricular assist device, prosthetic valve, valve clip or ring, endovascular graft, thrombus filter, pacemaker, defibrillator surface or lead, septal occluder, arterial appendage closure device, pulmonary artery catheter, venous catheter, or arterial catheter.

20. The method of claim 12, wherein the paracrine factor producing cells are stem cells.

21. A method for promoting regeneration of tissue in a subject, the method comprising:
- percutaneously delivering a bioreactor into the subject,
- the bioreactor being mounted on a catheter having at least one lumen and an infusion port,
- the bioreactor comprising an enclosed housing having a lumen,
- the catheter lumen connecting the infusion port with the housing lumen,
- the housing being impermeable to the paracrine factor producing cells and impermeable to immunological cells outside of the housing;
- the housing being permeable to growth factors and nutrients, but not the entry of cells, into the housing;
- wherein the housing includes pores sized to allow release of paracrine factors having a molecular weight greater than 500,000 Daltons from the paracrine factor producing cells out of the housing; and
- introducing cells that promote regeneration of tissue through the infusion port and into the housing lumen permitting the release of paracrine factors out of the housing to promote regeneration of the tissue.

22. The method of claim 21, wherein the cells produce paracrine and other factors.

23. The method of claim 22, further comprising continuously removing and/or replacing the cells, cell-conditioned media, paracrine and other factors, and/or other substances through the at least one catheter lumen to promote the maintenance and/or to enhance the performance of the cells.

24. The method of claim 22, further comprising intermittently removing and/or replacing the cells, cell-conditioned media, paracrine and other factors, and/or other substances through the at least one catheter lumen to promote the maintenance and/or to enhance the performance of the cells.

* * * * *